United States Patent [19]
Svaighert

[11] Patent Number: 5,226,991
[45] Date of Patent: Jul. 13, 1993

[54] METHOD OF FABRICATING AIRLAID ARTICLES AND APPARATUS FOR PERFORMING THE METHOD

[75] Inventor: Mike Svaighert, 3120 SW. 19th St., #144, Hallandale, Fla. 33009

[73] Assignees: Mike Svaighert; International Design & Mfg., Inc., both of Hallandale, Fla.

[21] Appl. No.: 774,071

[22] Filed: Oct. 9, 1991

[51] Int. Cl.$^5$ .............................................. B32B 31/00
[52] U.S. Cl. .................................. 156/62.2; 156/62.6; 156/251; 156/296; 156/515; 156/267; 19/148; 19/308; 425/80.1; 425/82.1
[58] Field of Search ............... 425/80.1, 82.1; 19/148, 19/308; 156/62.2, 62.6, 296, 251, 515, 267, 62.4; 264/121; 53/560, 454

[56] References Cited

U.S. PATENT DOCUMENTS

| | | | |
|---|---|---|---|
| 3,020,687 | 2/1962 | Joa | 156/267 |
| 4,571,924 | 2/1986 | Bahrani | 53/560 X |
| 4,592,708 | 6/1986 | Feist et al. | 425/80.1 |
| 4,605,404 | 8/1986 | Sneider | 604/389 X |
| 4,678,527 | 7/1987 | Ulman | 156/251 X |
| 4,795,455 | 1/1989 | Luceri et al. | 604/386 |

FOREIGN PATENT DOCUMENTS 2175620 12/1986 United Kingdom .................. 19/308

*Primary Examiner*—Jeff H. Aftergut
*Attorney, Agent, or Firm*—Herbert L. Lerner; Laurence A. Greenberg

[57] ABSTRACT

A method and an apparatus is used for forming airlaid articles such as diapers, sanitary napkins and the like. The apparatus includes an anvil drum with die cavities formed therein. The die cavities have foraminous bottom walls for drawing a stream of air-entrained fibrous fluff therethrough. A first material layer is laid on the anvil drum for covering some of the die cavities and is then deformed into the cavities. After a belt with opening corresponding to the die cavities has been laid on the first layer for protecting the sealing areas from fluff, an air stream with fibrous fluff is drawn through the first layer and through the foraminous bottom walls, thus pulling the first layer into the die cavities and causing the fluff to be deposited in the cavities. A second material layer is placed on the deposited fluff and glued or crimped to the first layer. A die-cutting roller then cuts the airlaid articles into the desired shape before the articles are removed from the anvil drum.

11 Claims, 8 Drawing Sheets

METHOD OF FABRICATING AIRLAID ARTICLES AND APPARATUS FOR PERFORMING THE METHOD

BACKGROUND OF THE INVENTION

1. Field of the Invention

The invention relates to an apparatus and a method for fabricating airlaid articles, and more particularly to a highly integrated apparatus for forming and dressing multidimensional fibrous pads such as sanitary napkins, diapers and the like.

2. Description of the Related Art

Several methods and devices for making sanitary napkins, diapers, and the like have been disclosed over the years, as reflected in the vast number of U.S. patents, some of which are listed below.

Most sanitary napkins utilize absorbent fibrous pads. The fibrous pad is obtained through the deposition of fluff on a drum-type air laying apparatus as shown in U.S. Pat. Nos. 1,950,765 and 2,073,329 to Winter in 1937 and in a great many patents issued in the following years. A more recent application of that basic principle is disclosed in U.S. Pat. Nos. 4,666,647 to Enloe et al and 4,592,708 to Feist et al.

Several fluff depositing, belt-type air laying apparatus are known as exemplified in U.S. Pat. Nos. 3,846,871 to Kolbach, 3,851,356 to Savich in 1974, 4,264,289 to Day, 4,375,447 to Chung, and many more.

From 1937 until the present both types of apparatus have been limited solely to obtaining a fibrous pad which is then transferred onto a conveyor where the dressing of the fluff, the sealing of the bottom and top material layers, and the cutting into the desired shape follow. Thus a finished product will appear at the end of an assembly line which includes several units and several conveyors.

Prior art patents disclose devices for manufacturing sanitary napkins and the like which do not possess the capability of creating a finished product directly on the anvil drum itself. Prior art teachings call for the cutting of the product into a given shape on an assembly line where the product continuously shifts left and right and thus the product cannot be cut evenly. Also, several transfers from the drum to the line and between different lines introduce inaccuracies and slow down the prior art devices quite substantially.

Finally, the prior art fluff preparing devices or pulp mills had certain shortcomings. It has always been necessary to use high-grade, and thus very expensive, pulp if good fluff was required. Good fluff, i.e. in which only few and very small chunks or knots of dry pulp are present in the fluff, is paramount in the manufacture of high quality sanitary napkins. Accordingly, only expensive dry pulp could previously be used in the manufacture of first grade napkins.

SUMMARY OF THE INVENTION

It is accordingly an object of the invention to provide a method and an apparatus for fabricating airlaid articles such as sanitary napkins and diapers, which overcome the hereinafore-mentioned disadvantages of the heretofore-known methods and devices of this general type and which allow for an accurate contour cutting of the product by preparing the finished product directly on the anvil drum, i.e. by immobilizing the dressed product in the airlay cavity through the step of cutting the product to its final shape. It is also an object of the invention to provide a device which allows an increase in the rotational speed of the drum in order to increase productivity, expressed by the number of usable products obtained per unit of time.

It is a further object of the invention to provide a dry pulp mill which allows the use of "low quality" pulp paper while being capable of producing highest grade absorbent fluff.

With the foregoing and other objects in view there is provided, in accordance with the invention, a method of making airlaid articles on an apparatus having an article deposition drum with die cavities formed therein, wherein the die cavities have a given shape and foraminous bottom walls for allowing a stream of air to pass therethrough, which comprises:

placing a first layer of material on the drum covering the die cavities;

guiding an airstream with fibrous fluff towards some of the die cavities covered with the first layer;

drawing air through the foraminous bottom walls of the die cavities for depositing the fibrous fluff on the first layer and holding the layer and the fluff in the cavities for conforming the layer and the fluff to the shape of the die cavities;

placing a second layer of material on the drum and covering the filled die cavities;

connecting the second and first layers for encapsulating the deposited fluff therebetween;

cutting the layers of material to a desired shape enclosing the deposited fibrous fluff for forming the airlaid article; and removing the airlaid article from the drum.

In accordance with a further feature of the invention, the deposited fibrous fluff is compacted in the die cavities prior to the step of placing the second layer.

In accordance with another feature of the invention, release tape is attached on the airlaid article prior to the steps of cutting and removing the article from the anvil drum.

With the objects of the invention in view, there is further provided, in accordance with the invention, an apparatus for forming airlaid articles of a given shape, comprising an anvil drum with a peripheral surface having die cavities formed therein defining the shape of the airlaid articles, foraminous bottom walls bordering the die cavities, means for placing a first material layer on the anvil drum for covering at least some of the die cavities, means for supplying and directing fibrous fluff to the anvil drum and for depositing the fibrous fluff on the first material layer, means for placing a second material layer on the anvil drum covering the first material layer and encapsulating fibrous fluff between the material layers, means for attaching the first and second material layers to one another, and means for cutting the airlaid articles to the given shape.

In accordance with an added feature of the invention, the means for supplying the fibrous fluff include a pulp mill for preparing fibrous fluff.

In accordance with an additional feature of the invention, the first material layer is formed of non-woven material and the second layer is plastic.

In accordance with again another, optional, feature of the invention, the attaching means is a heat crimping apparatus.

In accordance with again an added feature of the invention, the directing means include a suction fan communicating with the die cavities for drawing the fibrous fluff into the die cavities.

In accordance with again an additional feature of the invention, the cutting means are in the form of a die roller for die-cutting the airlaid articles.

With the objects of the invention in view there is further provided, in accordance with the invention, an improvement in an apparatus for forming airlaid articles of a given shape, which apparatus includes an anvil drum with a peripheral surface having die cavities formed therein, the die cavities defining the shape of the airlaid articles and foraminous bottom walls bordering the die cavities, a pulp supply means for supplying fibrous fluff and means for entraining the fibrous fluff in a flow of air, the improvement comprising means for placing a first material layer on the anvil drum for covering at least some of the die cavities, means for directing the air-entrained fibrous fluff to the anvil drum and for depositing the fibrous fluff on the first material layer, means for placing a second material layer on the anvil drum covering the first material layer and encapsulating fibrous fluff substantially in the die cavities and between the material layers, means for attaching the first and second material layers to one another, and means for die-cutting the airlaid articles into the given shape.

With the objects of the invention in view there is further provided, in accordance with the invention, a pulp mill apparatus, comprising a support structure, a rotating cylindrical rotor having a peripheral surface and a longitudinal axis, a multiplicity of milling teeth having a given length disposed on the surface for cutting pulp, a shaft for rotatably supporting the rotor on the support structure, and means for driving the rotor, the milling teeth each having a forward and a rearward edge as seen in an axial direction and being disposed in rings around the circumference of the rotor, the rings being axially spaced apart by substantially twice the length of the milling teeth and defining a plane perpendicular to the axial direction, the forward and the rearward edges of the milling teeth being disposed alternatingly in alignment with a respective one of the rings.

In accordance with yet an added feature of the invention, the milling teeth are disposed in substantially straight rows extending from the front to the rear as seen in a developed view of the peripheral surface, the rows defining a given angle with a parallel to the axial direction.

In accordance with a concomitant feature of the invention, the milling teeth are disposed on the rings at a given distance from one another, and wherein the given angle is defined as the inverse tangent of the given distance divided by the axial length of the rotor.

The present invention provides a machine and a method that converts dry pulp into fluff which is laid on a dressing material, which takes place in the cavities that are circumferentially spaced apart on a rotating anvil drum and wherein the fluff takes the desired shape with the aid of air drawn in through the foraminous bottom walls and later exhausted through a shaft from the machine.

Another aspect of the invention is that, prior to the fall of the fluff in the cavities on the anvil drum, a first layer of material is placed on the anvil drum and deformed into the cavity, which is then followed by the dressing of the material. Thereafter a second layer of material covers the fluff, still in the cavities on the anvil drum, and dresses it.

The invention further provides for the sealing of the dressing materials directly on the anvil drum. The process of cutting the material into the desired shape follows next, with the product still being present on the anvil drum. The finished product is lifted off the anvil drum with the aid of a vacuum pick-up conveyor. The method and apparatus of the present invention go beyond the prior art devices in that a finished product is produced directly on the anvil drum, thus eliminating the need for an assembly line with units to accomplish any steps outside the apparatus proper.

Besides the above-mentioned advantages offered by the present invention such as the precise contour cutting of the material into a given shape and the increase of production per unit time due to the increased rotary speed of the anvil drum, several additional advantages of the present invention are:

a) The apparatus is of a compact size (5-6 ft. in length), while the prior art devices all are in the range of 40-60 ft.
b) Several units, all the gear boxes for driving the units and all the conveyors that feed the units as they are known from prior art teachings have been eliminated from the disclosed apparatus. Accordingly, the cost of the apparatus is substantially reduced without sacrificing quality.
c) The apparatus can be supervised by a single operator, with all of the components being easily accessible and serviceable.

Other features which are considered as characteristic for the invention are set forth in the appended claims.

Although the invention is illustrated and described herein as embodied in a method and apparatus for fabricating air-laid articles, it is nevertheless not intended to be limited to the details shown, since various modifications and structural changes may be made therein without departing from the spirit of the invention and within the scope and range of equivalents of the claims. It is noted that the term "sanitary napkin" applies to all equivalent products such as diapers and the like.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
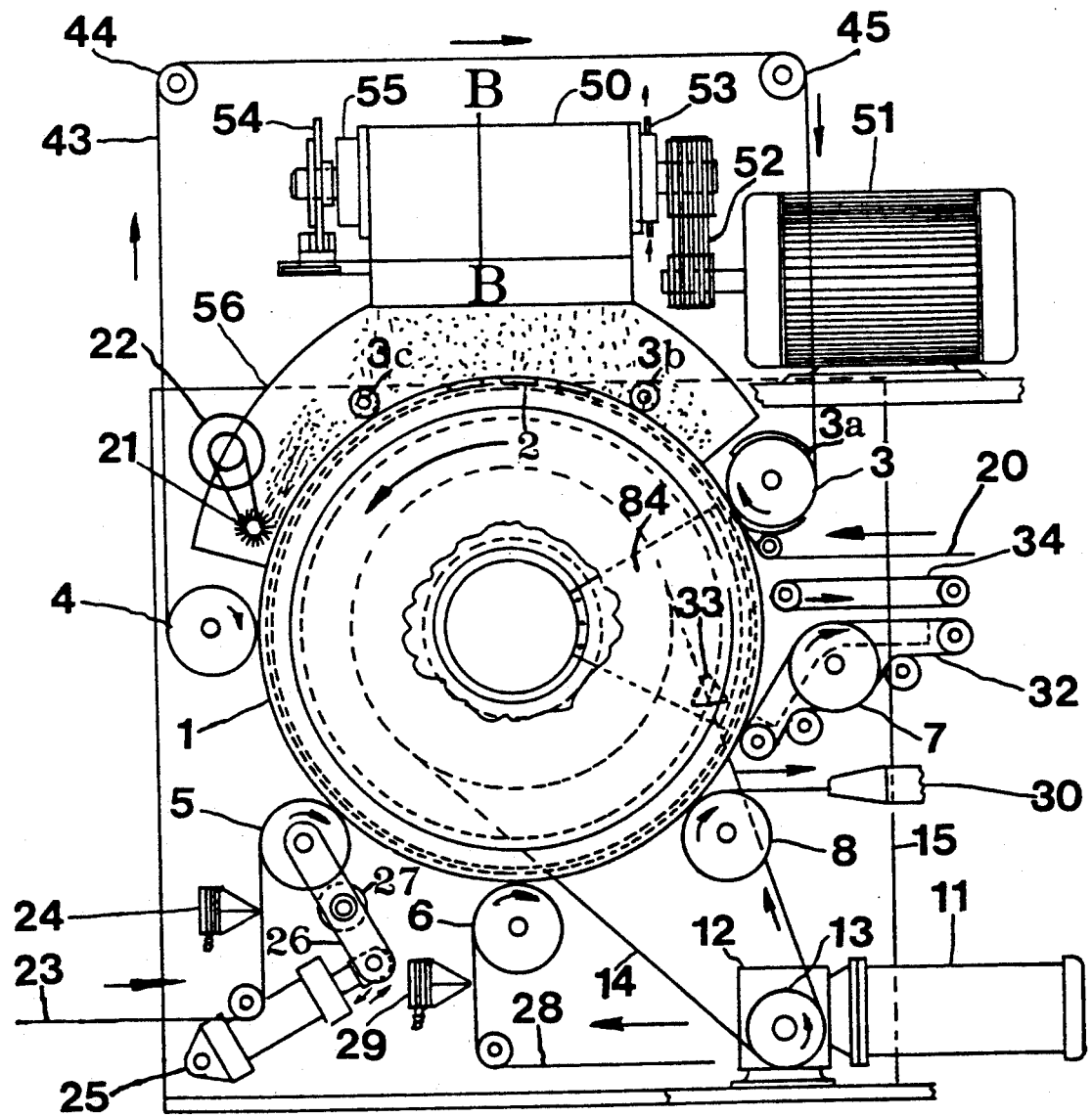
FIG. 1 is a diagrammatic, front-elevational view of an apparatus according to the invention.
Figure 8:
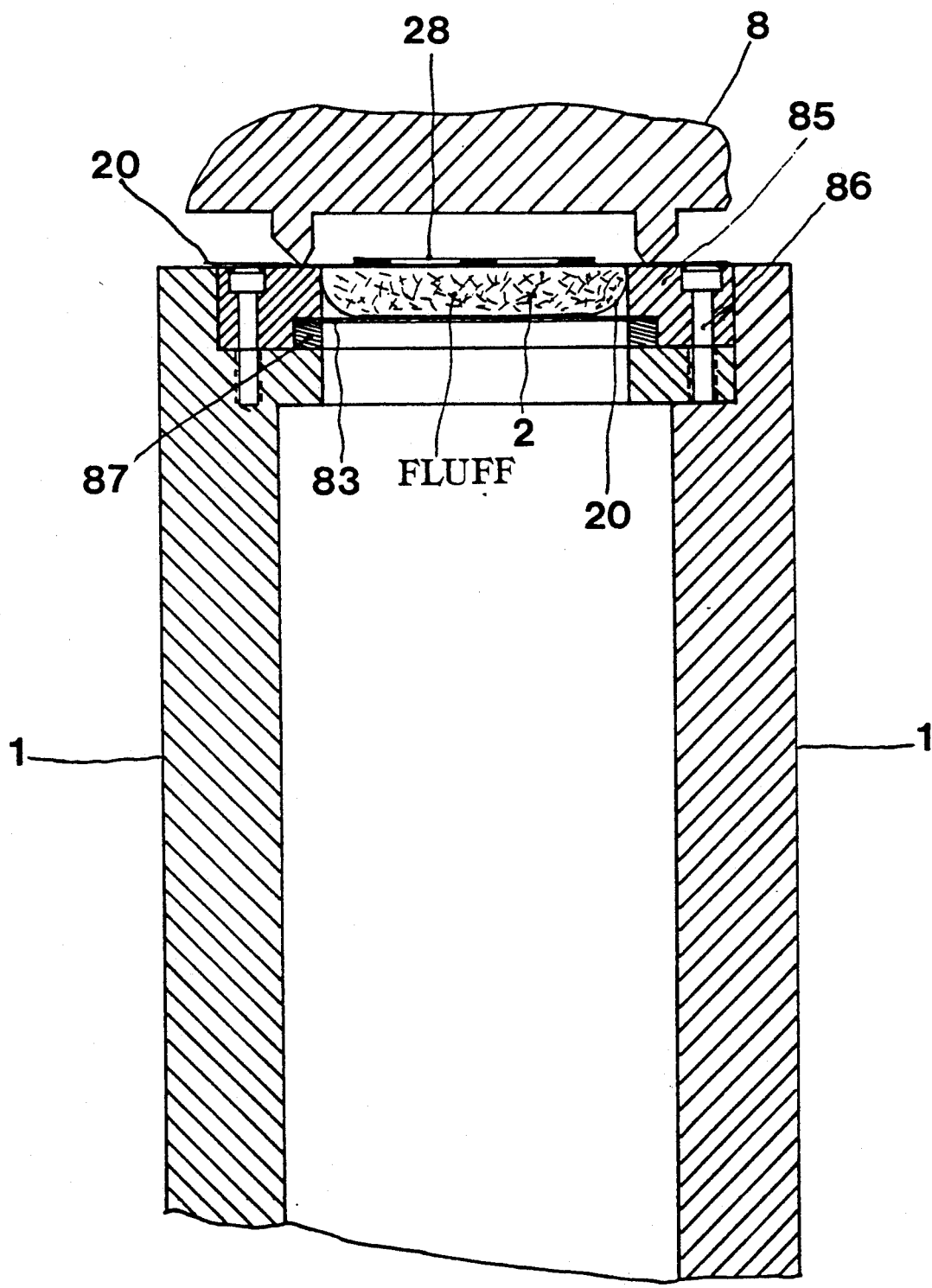
FIG. 8 is a fragmentary, cross-sectional view of a rotary die cutting the product in an anvil die on an anvil drum.

Referring now to the figures of the drawing in detail and first, particularly, to FIG. 1 thereof, there is seen an airlaid article manufacturing apparatus used in the fabrication of various fibrous articles such as sanitary napkins, diapers and the like. An anvil drum 1 includes depressions or die cavities 2, some of which are indicated in the drawings, distributed about the circumference of the drum 1. The anvil drum 1 of a preferred embodiment of the invention presently has 48 cavities 2 in as many dies, as shown in FIG. 8, but other numbers are equally possible, depending on the size of the product and the drum. A number of guide rollers 3-7, the structure and purpose of which will be explained below, are disposed about the anvil drum 1.

The anvil drum 1 rotates counter-clockwise and is driven by a motor 11. A gear box 12 connects the motor 11 to a sprocket or pulley 13 via which a timing belt 14 finally connects the motor 11 to the drum 1.

Disposed above the anvil drum 1 and its related components can be seen a compact mill 50 for preparing absorbent, fibrous fluff from dry pulp. The mill 50 is driven by a motor 51, via a belt 52. Bearing cooling system 53 and 55, as well as a brake assembly 54 will be described in detail with reference to FIG. 4.

After the mill 50 prepares the fibrous fluff, a vacuum created inside the anvil drum 1 draws the fluff into a fluff distribution chamber 56. The chamber 56 is enclosed with plexiglass or similar material, since it is advantageous to keep the airlaying process visible to the operator.

A continuous strip of non-woven material 20 enters from the right in FIG. 1 and is placed on the anvil drum 1 by the guide roller 3 at about 2 o'clock. The roller guide, advantageously has two die protrusions 3a which engage into the cavities 2 on the drum, and thus deform the non-woven material 20 into the cavities 2. The width of the strip 20 is slightly greater than the length of the finished product. Once the apparatus is primed, i.e. the material 20 covers the anvil drum 1 and particularly the deposition die cavities 2 between the rollers 3 and 4, the latter being disposed at about 9 o'clock, the fluff may enter the chamber 56. The fibrous fluff is now transferred and drawn into the airlay cavities 2 with the aid of a vaccum in the anvil drum 1 and it is deposited on the first layer of material 20. The material 20 is thus drawn into and held in the cavities 2 by vacuum aspiration and thus takes the shape of the cavities 2.

While the non-woven material 20 is located between the rollers 3 and 4 in a deposition or airlay chamber 56, the sealing areas on the non-woven material 20 are protected by a belt 43 which travels about the rollers 3 and 4 and reversal rollers 44 and 45. The belt 43 is adapted to the die cavities 2 on the anvil drum 1, thus allowing the fluff to be deposited in the cavities 2 while protecting the marginal areas from being soiled with fluff, which would impair the sealing which is to follow. The exact positioning of the belt 43 is timed by means of non-illustrated sprockets on the anvil drum 1. This is similar to a tractor feed sprocket system on continuous-feed computer printers. The correct synchronization of the belt 4 is further assured by the two die protrusions 3a on the roller 3.

The fluff is compacted into the cavities 2 by two compactor rollers 3b and 3c which are driven by friction with the belt 43. As the die cavities 2 are about to leave the airlay chamber 56 at about 10 o'clock, extraneous fluff is brushed off by a brush 21, which is driven by a motor 22. Now the compacted, filled cavities 2 travel from airlay chamber 56 to the next application step.

Cover material 23 enters from the bottom left of FIG. 1, passes by and comes into contact with a glue head or glue applicator 24, rolls on the guide roller 5 and is thus placed on the anvil drum 1, on top of the filled dies 2. The roller 5, which rotates at the same peripheral speed as the anvil drum 1, presses the cover material onto the anvil drum, and thus over the first layer of material 20, encapsulating or captivating the formed fluff in between. A contour seal is thus obtained between the first material layer 20 and the cover material layer 23.

In an alternative embodiment, heat crimping is used instead of a glue contour seal. For that purpose, the roller 5 is equipped with non-illustrated heating means and its circumferential surface carries embossing dies, as they are commonly used in heat crimping. One possible means for heating is a heat cartridge to be inserted in the roller 5. It is important, in this context, that the plastic material 23 is not melted too early on the roller 5. Accordingly, the material 23 is directed about non-illustrated auxiliary rollers such that it enters the crimping zone between the roller 5 and the anvil drum 1 nearly tangentially. Also, in the case of heat crimping, the glue applicator 24 may be omitted.

As seen in FIG. 1, the pressure by which the guide roller 5 is force against the anvil drum 1 is defined by the action of a pneumatic or hydraulic piston 25 which acts on a lever 26 and thus swivels the guide roller 5 about a swivel point 27.

Release paper 28 enters the apparatus at the bottom of FIG. 1, travels by a glue applicator 29, and is then placed on the anvil drum 1 by the roller 6, at about 6 o'clock, and is thus glued to the cover layer 23.

The product remains in the cavities 2 on the anvil drum 1 when it is taken to the next operation at the cutter roller or rotary die 8. The product is now cut into its final shape, i.e. around the glued edges surrounding the compacted fibrous fluff. The trimmed material around the edges is vacuumed off through tubing 30 and deposited in a non-illustrated container.

The final product is kept in the cavities 2 by the suction vacuum applied on the inside of the anvil drum 1. Once the cavity 2 has passed by a guide roller 31, which is a part of a conveyor belt assembly including a reversal roller 32 and the guide roller 7, an air jet nozzle 33 blows the product out of the anvil cavity 2 and onto the conveyor assembly. The product now travels on the conveyor assembly around the guide roller 7, and leaves the apparatus at about 3 o'clock. Another conveyor 34 ensures that the product indeed leaves the apparatus before the non-woven material 20 is placed onto the anvil drum 1 at 2 o'clock.

Disposed inside a main housing 15 of the airlay apparatus is a main gear housing or column 38 which has six or more shaft exits for driving the rollers 3-8; all of these rollers rotate at substantially the same circumferential speed as the anvil drum 1.

Figure 2:
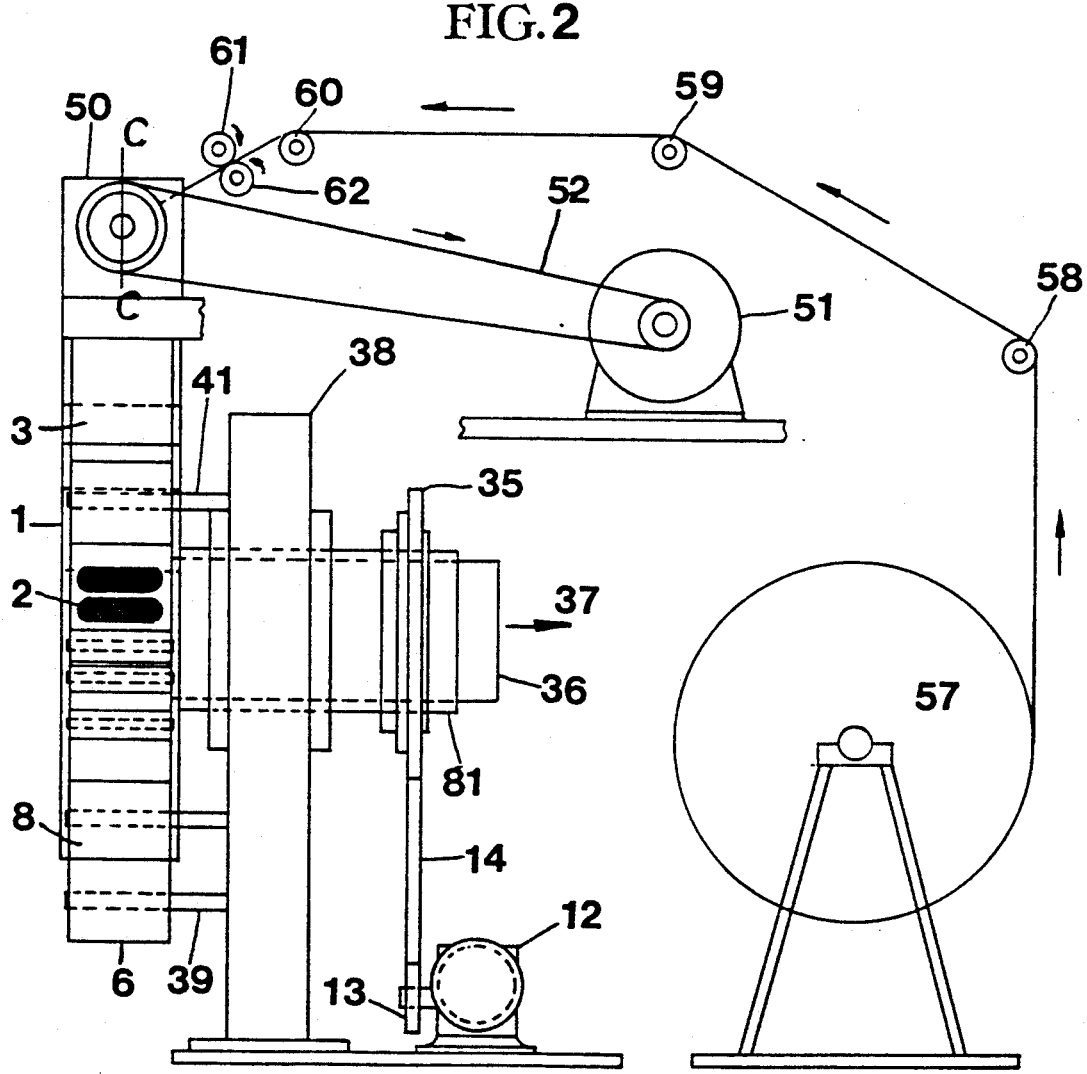
FIG. 2 is a side-elevational view of the apparatus.

As seen in FIG. 2, material 57, which is dry pulp in sheet form on rollers, is guided by a number of cylindrical rollers 58-60 to a pair of clamping rollers 61 and 62 and is then fed into the compact mill 50, where the fibrous fluff is produced.

In the embodiment as shown, forty-eight dies 85 are distributed on the exterior of the anvil drum 1. The timing belt 14 drives the anvil drum 1 via a sprocket wheel 35, which is permanently connected to a rotating shaft 81. Suction is applied to the anvil drum interior through a stationary shaft 36, and the air is evacuated along an arrow 37.

The rotating shaft 81 of the anvil drum 1 is mounted and counter-balanced in the column 38. Also mounted and driven from the column 38 are drive shafts 39–41 of the rollers 6, 8 and 3, respectively, as well as the non-illustrated shafts of the rollers 4, 5 and 7.

Figure 3:
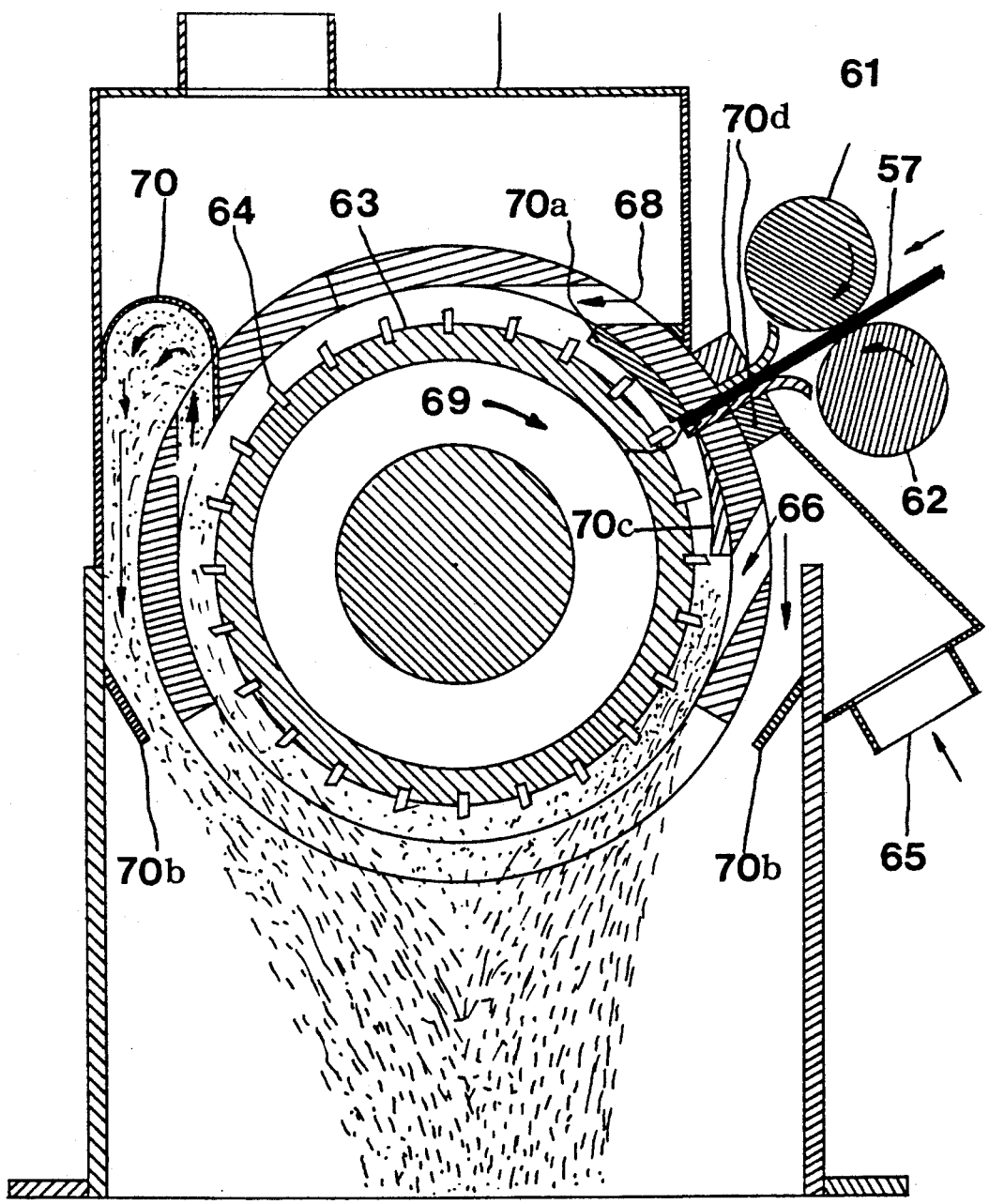
FIG. 3 is a cross-sectional view taken along the line B—B of FIG. 1, showing the mill chamber, mill housing, mill rotor, pulp and air intake system.

As can be seen in FIG. 3, the dry pulp sheet 57 enters the mill 50 after passing through the rollers 61 and 62 and face a fiberdizing rotor 63 virtually perpendicularly. The rotor 63 has over 4000 carbide teeth 64 distributed in a given pattern about its surface for fiberdizing the pulp 57 and creating the fibrous fluff. Air is taken into the mill housing at an intake 65 and travels along arrows 66, as well as at an intake 67 which air stream travels into the rotor chamber at and arrow 68.

As shown by an arrow 69, the rotor 63 rotates clockwise. The airstream 66, which enters the rotor chamber tangentially in the direction of rotation, blows the fibrous fluff towards the bottom opening of the mill leading to the chamber 56. The airstream 68 enters tangentially but in a direction opposite the rotation of the milling rotor 63. This is to ensure that any fibers remaining on the carbide teeth 64 are blown off, and leave the rotor chamber at an exit 70. The blowout stream 68 ensures the cleaning of the rotor and thus helps prevent overheating and reduces fire hazard in the pulp mill 50.

A stop 70a for preventing milled pulp buildup on the drum 63 and several stream guides 70b ensure the proper operation of the device in a full load environment. Finally, it has been found advantageous for a stop 70c to prevent larger pieces of pulp from remaining in the air space surrounding the pulp rotor. Accordingly, any larger pieces of pulp are forced among the milling teeth 64 for further milling. Two entry guides 70d ensure relatively air-tight entry of the dry pulp into the mill. Prior art devices would have a screen extending between the guides 70b. The stop 70c, which has a tolering distance from the carbide teeth of approximately 0.002–0.005 inches, and the stop 70a eliminate the requirement for such a screen.

Figure 4:
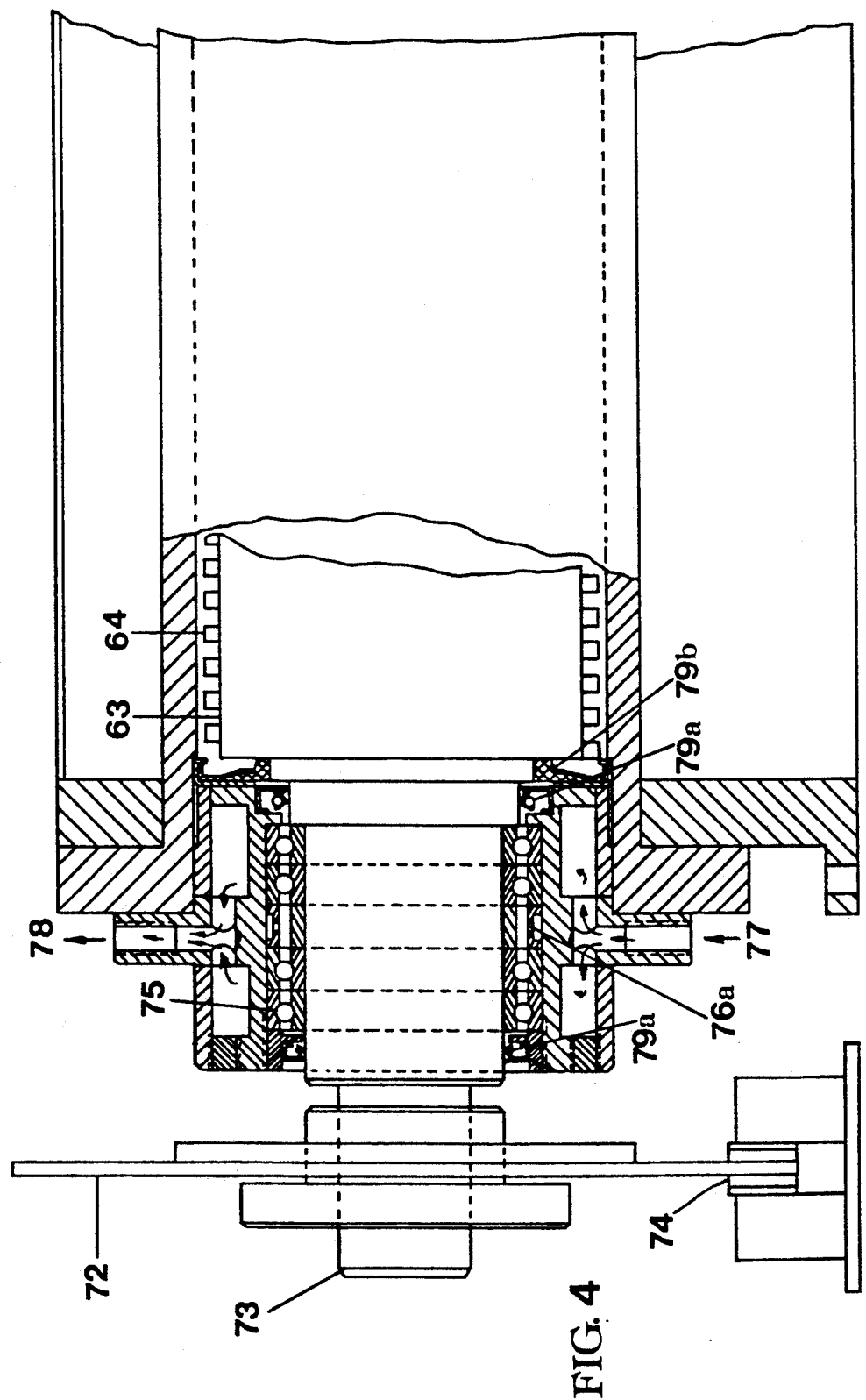
FIG. 4 is a partly broken-away longitudinal-sectional view taken along the line C—C of FIG. 2, showing the rotor, bearing housing, and cooling system of the pulp mill.

FIG. 4 shows a cross section through the milling rotor 63 and its lubricating and braking systems. The milling rotor 63 of the preferred embodiment rotates at approximately 3000 to 5000 rpm. However, the mechanical stability should allow about 7000 rpm and such speeds have been tested.

The main advantage of the mill as it is disclosed and claimed is its ability to produce superior fluff from low quality, and thus inexpensive, paper. In this respect it is noted that "superior fluff" is defined as having maximum length of fiber, i.e. minimal fiber damage, and minimum knot content, i.e. only very few and very small heavier pieces of dry pulp.

It is sometimes necessary to very quickly stop the mill. For that purpose, a disk braking system is provided which is basically known. A braking disk 72 is attached to a central bearing shaft extension 73 of the rotor 63. Braking calipers 74 which are provided are controlled and actuated in a conventional fashion. Bearings 75 are disposed within a bearing cartridge, which has a lubrication chamber 76a and a coolant chamber 76b. Coolant, such as air conditioner fluid, enters the circumferential chamber 76b at an arrow 77 and leaves the chamber 76b at an arrow 78. Due to the weight of the rotor 6 with its carbide teeth 64 and the higher circumferential speed required, the proper functioning of the bearings is of utmost importance. It has been found that rotor bearings as they are used in aircraft technology are quite satisfactory in this respect, and reference is herewith made to the pertinent literature. A circumferential rubber seal 79a ensures that the grease remains in the lubrication chamber 76a. Any leaking of lubricant into the milling chamber is avoided by a safety felt seal 79b and thus mixing of the fluff with the lubricant is avoided.

Figure 5:
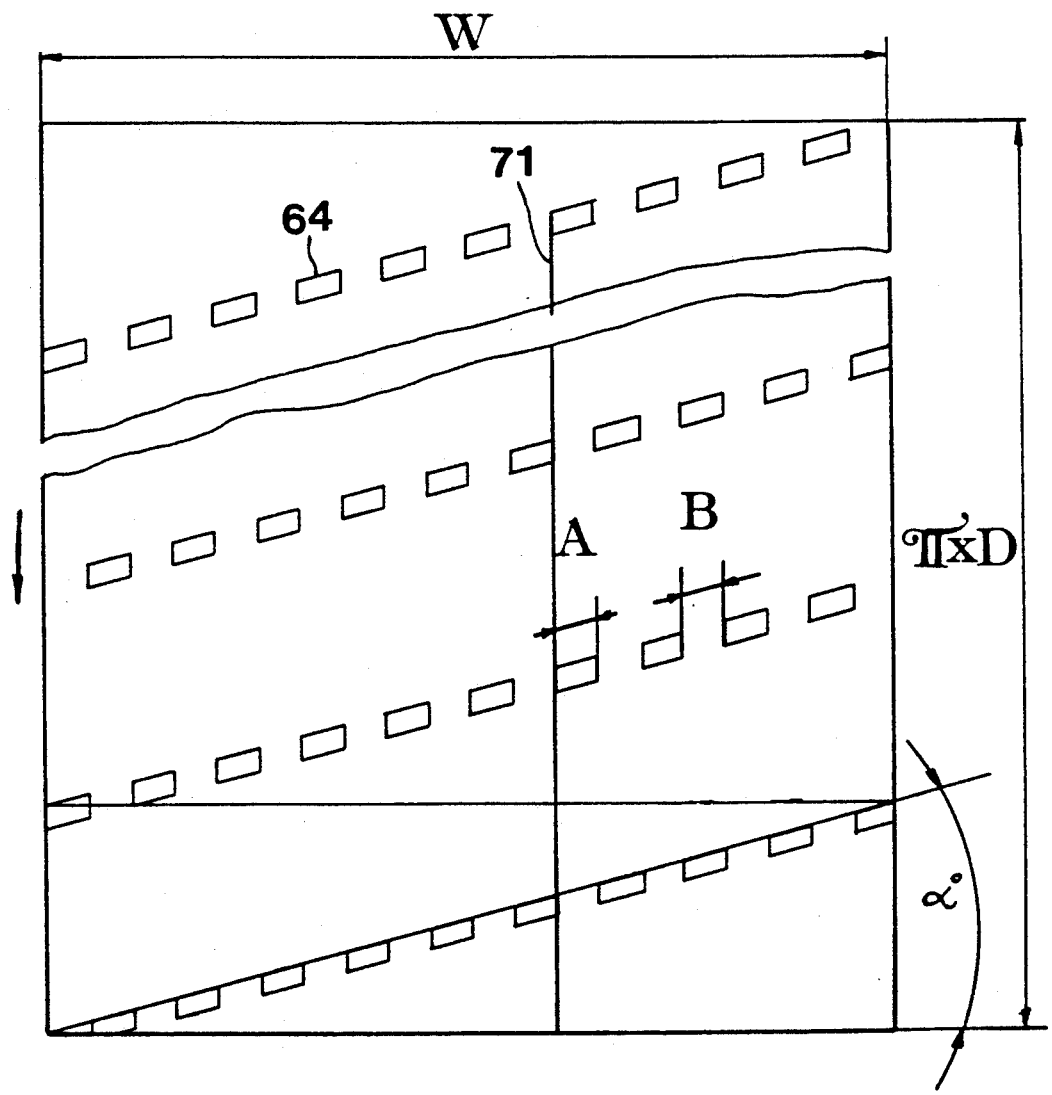
FIG. 5 is a fragmentary, developed view of the surface of the axial rotary cylindrical disintegrator, showing a possible distribution of disintegrator teeth.

FIG. 5 illustrates a preferred distribution of the milling teeth 64 on the rotor 63. Accordingly, the teeth 64 are disposed along a circumferential line in alternating fashion, i.e. one tooth on the left of the line, the next one on the right, etc. The teeth 64 are further offset in an axial direction by an angle $\alpha$, so that the location of the left-most tooth of one row coincides axially with the right-most tooth of the adjacent row of teeth. With reference to a developed view of the peripheral surface of the rotor 63, the angle $\alpha$ is defined as the inverse tangent of the circumferential distance between the teeth 64 divided by the axial length of the rotor. This distribution ensures proper milling of the pulp as well as the least possible strain on the rotor bearings.

Figure 6:
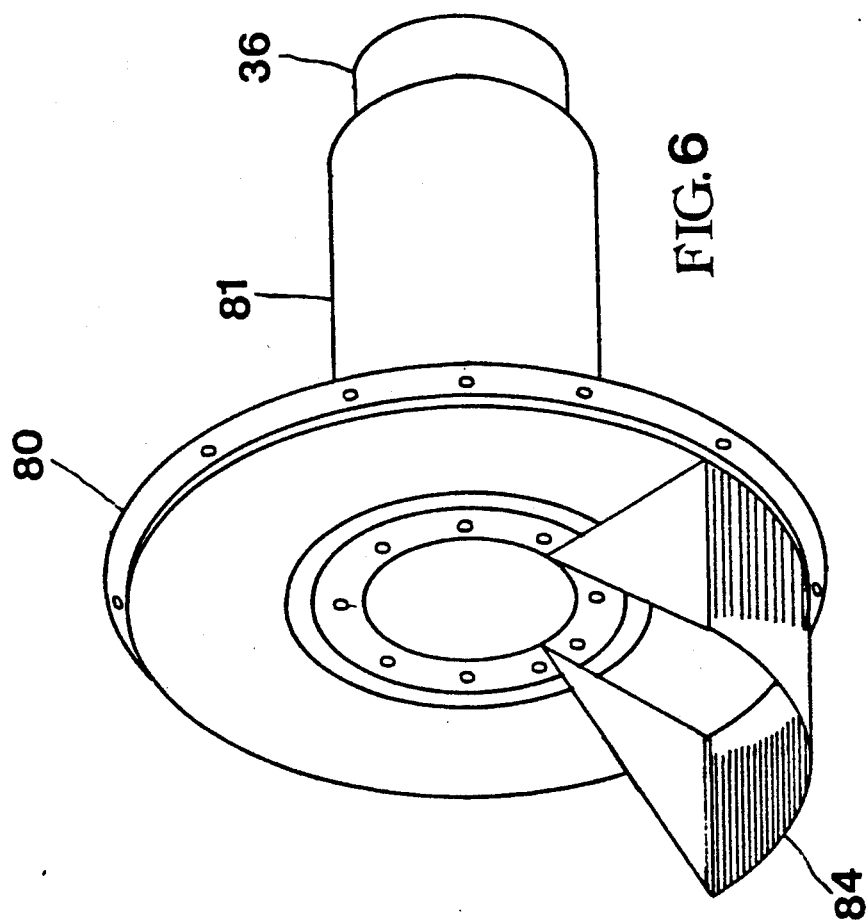
FIG. 6 is an exploded perspective view showing an anvil drum die assembly, main shaft, inner stationary shaft, and vacuum chamber.
Figure 6:
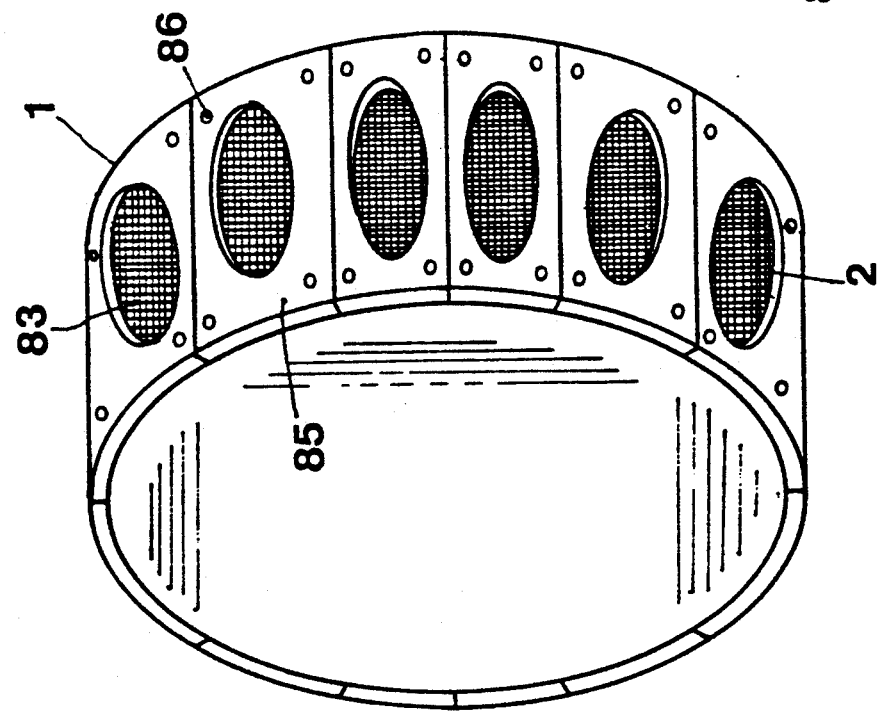

As shown in FIG. 6, a number of anvil dies 85 are mounted on the anvil drum 1. In the preferred embodiment, there are 48 dies 85 mounted on the drum 1. The anvil drum die assembly can be removed from a back wall 80, which is permanently connected to the rotating shaft 81 and the stationary vacuum shaft 36. A foraminous mesh 83 is placed at the bottom of the die cavities 2 which approximately defines the shape of the finished product. It is again noted that the bottom material or non-woven 20 is first placed on the drum 1. The suction of the vacuum on the inside of the drum draws the non-woven 20 into the cavities towards the mesh 83. The suction through the mesh 83 and through the non-woven 20 draws fluff-entrained air into the cavity 2 and the fluff is thus deposited in the cavity 2.

In an alternative mode of operation, different dies may be mounted on the anvil drum 1, so that it is even conceivable that differently shaped products could be produced in one production run.

A segment 84 of approximately ¼ inch felt is rigidly connected to the stationary shaft 36. The segment 84, which is also indicated in FIG. 1, ensures that the vacuum draft acting on the cavities 2 does not act on those cavities which are located at any time between the location where the finished product leaves the anvil drum 1 and the location where the non-woven material 20 is placed on the anvil drum 1. Accordingly, as seen in FIG. 1, the segment 84 extends from about 2 to about 4 o'clock.

Figure 7:
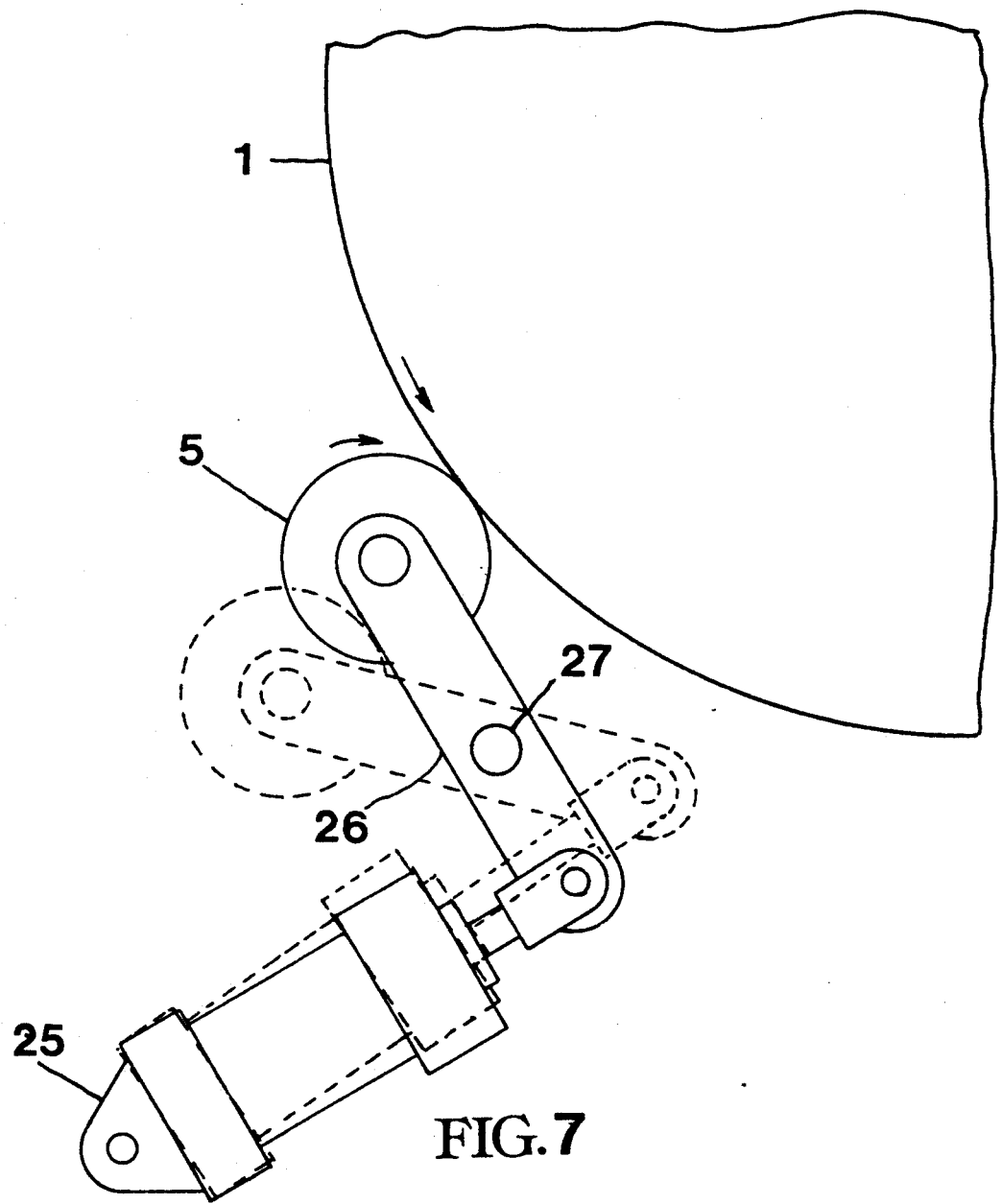
FIG. 7 is a fragmentary view showing the engaging system of the rotary die, and other rotating units on the anvil drum.

The pneumatic system shown in FIG. 7 may be used for any of the rollers 4, 5, 6 and 8. Accordingly, although FIGS. 1 and 7 show the use thereof with the applicator roller 5, the system may equivalently be used with the deformer roller 3, the release paper roller 6, the heat crimping assembly, and the rotary die 8.

In fact, the use of the pneumatic system (equivalently a hydraulic system) is quite advantageous over any prior art apparatus. In the prior art, the shafts of rollers such as rollers 3–8 required the mounting on a back as well as a front plate. The present invention makes it possible to dispense of the front plate for the apparatus, since the roller shafts need not be secured thereto. This provides for easy servicability and accessibility to all of the components without requiring the temporary removal of a front plate.

As better shown in FIG. 8, the anvil dies 85 are mounted on the anvil drum 1 by means of bolts 86. When the cavities 2 travel by the rotary die 8, the two layers of non-woven material 20 and cover material or poly 23, which have been crimped together, and release paper has been added 6, are now cut. The rotary die 8 cuts to exactly the shape desired and must thus be adapted to the shape of the anvil cavities 2 in the anvil dies 85. Spacers 87 are used to define the thickness of the finished product, i.e. to define the distance of the foraminous bottom walls 83 from the surface of the anvil drum 1.

I claim:

1. A method of making airlaid articles on an apparatus having an article deposition drum with die cavities formed therein, wherein the die cavities have a given shape and foraminous bottom walls for allowing a stream of air to pass therethrough, which comprises:
    placing a first layer of material on the drum covering the die cavities;
    covering the first layer with a belt having cutouts corresponding to the die cavities on the drum;
    guiding an airstream with fibrous fluff towards some of the die cavities covered with the first layer;
    protecting, with the belt, the first layer against depositing fluff in areas outside the die cavities where a second layer of material is to be connected to the first layer;
    drawing air through the foraminous bottom walls of the die cavities for depositing the fibrous fluff on the first layer and holding the layer and the fluff in the cavities for conforming the layer and the fluff to the shape of the die cavities;
    placing a second layer of material on the drum and covering the filled die cavities;
    connecting the second and first layers for encapsulating the deposited fluff therebetween;
    cutting the layers of material to a desired shape enclosing the deposited fibrous fluff for forming the airlaid article; and
    removing the airlaid article from the drum.

2. The method according to claim 1, which further comprises compacting the deposited fibrous fluff in the die cavities prior to the step of placing the second layer.

3. The method according to claim 1, which further comprises attaching release tape on the airfield article prior to the step of cutting.

4. The method according to claim 1, which further comprises deforming the first layer of material by conforming the layer to the die cavities on the drum.

5. An apparatus for forming airlaid articles of a given shape, comprising an anvil drum with a peripheral surface having die cavities formed therein defining the shape of the airlaid articles, foraminous bottom walls bordering said die cavities, means for placing a first material layer on said anvil drum for covering at least some of said die cavities, means for supplying and directing fibrous fluff to said anvil drum and for depositing the fibrous fluff on the first material layer, means for placing a second material layer on said anvil drum covering the first material layer and encapsulating fibrous fluff between the material layers, means for attaching the first and second material layers to one another, means for cutting the airlaid articles to the given shape, and means for protecting the first layer from depositing fluff except in said die cavities, said protecting means being in the form of a continuous belt having cutouts formed therein corresponding to said die cavities on said drum.

6. The apparatus according to claim 5, including means for attaching release paper to the airlaid articles.

7. The apparatus according to claim 5, wherein said means for supplying the fibrous fluff includes a pulp mill for preparing fibrous fluff and a suction fan communicating with the die cavities for drawing the air-entrained fibrous fluff in said die cavities.

8. The apparatus according to claim 5, wherein said attaching means is a heat crimping apparatus.

9. The apparatus according to claim 5, wherein said attaching means is a glue sealing apparatus.

10. The apparatus according to claim 5, wherein said cutting means are in the form of a die roller for die-cutting the airlaid articles.

11. In an apparatus for forming airlaid articles of a given shape, which apparatus includes an anvil drum with a peripheral surface having die cavities formed therein, the die cavities defining the shape of the airlaid articles and foraminous bottom walls bordering the die cavities, a pulp supply means for supplying fibrous fluff and means for entraining the fibrous fluff in a flow of air, the improvement comprising means for placing a first material layer on said anvil drum for covering at least some of said die cavities, means for directing the air-entrained fibrous fluff to said anvil drum and for depositing the fibrous fluff on the first material layer, means for placing a second material layer on said anvil drum covering the first material layer and encapsulating fibrous fluff substantially in the die cavities and between the material layers, means for protecting the first layer from depositing fluff except in said die cavities, said protecting means being in the form of a continuous belt having cutouts formed therein corresponding to said die cavities on said drum, and means for attaching the first and second material layers to one another, and means for cutting the airlaid articles into the given shape.

* * * * *